(12) United States Patent
Desmedt et al.

(10) Patent No.: US 7,764,984 B2
(45) Date of Patent: Jul. 27, 2010

(54) APPARATUS AND METHOD FOR NAVIGATING AN INSTRUMENT THROUGH AN ANATOMICAL STRUCTURE

(75) Inventors: Paul Antoon Cyriel Desmedt, Eindhoven (NL); Shirley Antoinette Maurice Baert, Den Bosch (NL); Wiro Joep Niessen, Driebergen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1055 days.

(21) Appl. No.: 10/563,934

(22) PCT Filed: Jul. 7, 2004

(86) PCT No.: PCT/IB2004/051147

§ 371 (c)(1),
(2), (4) Date: Apr. 28, 2006

(87) PCT Pub. No.: WO2005/004724

PCT Pub. Date: Jan. 20, 2005

(65) Prior Publication Data
US 2006/0235287 A1 Oct. 19, 2006

(51) Int. Cl.
*A61B 5/05* (2006.01)
(52) U.S. Cl. ........................... 600/424; 600/425
(58) Field of Classification Search .......... 600/424, 600/425, 427; 378/21–27
See application file for complete search history.

(56) References Cited

U.S. PATENT DOCUMENTS

| 5,274,551 | A | 12/1993 | Corby, Jr. |
| 6,144,759 | A | 11/2000 | Weese et al. |
| 6,317,621 | B1 * | 11/2001 | Graumann et al. .......... 600/424 |
| 6,351,513 | B1 | 2/2002 | Bani-Hashemi et al. |
| 6,542,770 | B2 | 4/2003 | Zylka et al. |
| 7,050,844 | B2 * | 5/2006 | Strobel ....................... 600/424 |
| 7,302,286 | B2 * | 11/2007 | Camus et al. ............... 600/407 |
| 2003/0181809 | A1 * | 9/2003 | Hall et al. ................... 600/425 |

FOREIGN PATENT DOCUMENTS

| WO | 0187136 A | 11/2001 |
| WO | 02091925 A | 11/2002 |

* cited by examiner

*Primary Examiner*—Long V Le
*Assistant Examiner*—Jacqueline Cheng

(57) ABSTRACT

Apparatus for navigating an instrument through an anatomical structure of a patient's body volume, comprising a table for supporting the patient and at least a first C-arm having a first X-ray source and a first X-ray detector for acquiring a first series of 2D-images of the instrument while maneuvering through said anatomical structure, and further comprising a processing unit for the images which unit connects to a memory device, whereby the memory device holds pre-determined 3D-images of the patient's anatomical structure, and the processing unit is arranged for processing the 2D-images of the instrument and the 3D-images of the anatomical structure so as to provide merged 3D-images of the instrument that in use maneuvers through said anatomical structure.

12 Claims, 5 Drawing Sheets

APPARATUS AND METHOD FOR NAVIGATING AN INSTRUMENT THROUGH AN ANATOMICAL STRUCTURE

The invention relates to an apparatus and method for navigating an instrument through an anatomical structure of a patient's body volume, comprising a table for supporting the patient and at least a first C-arm having a X-ray source and a X-ray detector for acquiring a first series of 2D-images of the instrument whilst manoeuvering through said anatomical structure, and further comprising a processing unit for the images which unit connects to a memory device, whereby the memory device holds pre-determined 3D-images of the patient's anatomical structure, and the processing unit is arranged for processing the 2D-images of the instrument and the 3D-images of the anatomical structure so as to provide merged 3D-images of the instrument that in use manoeuvers through said anatomical structure.

Such an apparatus and method are known from U.S. Pat. No. 6,351,513.

In the known apparatus and method 3D-images of a patient's anatomical structure, in particular the patient's vascular structure are obtained by 3D-angiography, magnetic resonance imaging or computer tomography imaging. These 3D-images are of comparatively high resolution and quality.

To alleviate navigational difficulties that the radiologist experiences when a medical instrument such as a catheter is pushed through said vascular structure to a region of interest, U.S. Pat. No. 6,351,513 teaches to apply real time 2D imaging of the instrument whilst maneuvering through the vascular structure and merging the 2D-image of the instrument with the predetermined 3D-images of the vascular structure. Since the catheter is moving through a vessel the catheter must according to U.S. Pat. No. 6,351,513 actually lie in 3D space, somewhere on a "sheaf" which is a surface formed by taking a line (a catheter) and keep sweeping along the length of the catheter. This generates a surface and the catheter can be anywhere on that surface. Since we know that the catheter is moving through the vessel which is a 3D structure, the intersection of this surface with the pre-stored 3D reconstruction data, gives the location of the catheter. U.S. Pat. No. 6,351,513 teaches: if the 3D reconstruction of the vessels is known (i.e. from the 3D-angiography reconstruction) the position of the catheter is also known since it is confined within the reconstructed vessels.

Several problems attach to the method and apparatus according to U.S. Pat. No. 6,351,513. As a first problem the known art does not take into account that the position of the C-arm is not always calibrated, causing that inaccuracies occur and correspondence is lacking between the priorly acquired 3D-images of the vascular structure and the later acquired 2D-images of the instrument.

A second problem is that during imaging the patient may intentionally or unintentionally move. Even movement due to beating of the heart and breathing may give rise to unacceptable inaccuracies.

A third problem is that the radiologist may elect to move the table on which the patient is laying in an effort to improve his view at the instrument during manoeuvering.

All said problems may result in discrepancies in the merged images of the instrument and the vascular structure making same unreliable. Although hereabove and also hereafter at some places reference is made to a patient's vascular structure, the invention is not restricted to this application but applies in general to a patient's anatomical structure. The reference to the vascular structure is however particularly useful in understanding the invention.

With the apparatus and method according to the invention it is aimed to reduce or circumvent the above-mentioned problems.

To this end the apparatus according to the invention is characterized in that the processing unit is arranged to carry out a 2D-3D registration to relate the coordinates of the 2D-images of the instrument to the coordinates of the 3D-images of the anatomical structure prior to providing the merged 3D-images of the instrument and the anatomical structure. It is to be noted that although usually the images of the anatomical structure are obtained prior to the imaging of the instrument, the 3D-images of the anatomical structure may also be obtained during the intervention with the instrument. In the first situation, i.e. when the acquisition of images of the anatomical structure has been done prior to the imaging of the instrument, it is desirable to immediately precede the imaging of the instrument by a short imaging of the anatomical structure. This allows for registering the images taken during this session with the coordinates of the earlier recorded 3D-images of the anatomical structure.

A first preferred embodiment of the apparatus according to the invention is characterized it comprises a second C-arm with a X-ray source and a X-ray detector for acquiring a second series of 2D-images simultaneously with the first series of 2D-images, and that the processing unit is arranged to carry out the 2D-3D registration on both the first series and the second series of 2D-images of the instrument, and that the processing unit is arranged to derive thereafter a 3D-image of the instrument based on said first and second series of 2D-images and to merge said 3D-image of the instrument with the 3D-images of the anatomical structure. This embodiment provides the advantage that the 3D-image of the instrument and in particular its location within the patient's body volume can be established independently from the priorly established 3D-image of the patient's anatomical structure. This results in higher accuracy of the instrument's actual positioning in the patient's body.

Consistent with the above the method according to the invention is characterized in that the 2D-images of the instrument are registered with the 3D-images of the anatomical structure prior to providing the merged 3D-images of the instrument and the anatomical structure, and that in a preferred embodiment a second series of 2D-images is acquired simultaneously with the first series of 2D-images of the instrument but from a different angle, whereby both the first series and the second series of 2D-images of the instrument are registered with the 3D-images of the anatomical structure followed by deriving from the first and second series of 2D-images a series of 3D-images of the instrument, and that the 3D-images of the instrument are merged with the 3D-images of the anatomical structure.

A second more preferred embodiment of the apparatus according to the invention is characterized in that the memory device holds a pre-determined 3D-model representation of the instrument and that the processing unit is arranged to carry out a 2D-3D registration to relate the coordinates of the 3D-model representation with the coordinates of the 2D-images of the instrument, and that the processing unit is further arranged to calculate 2D-model images of the instrument corresponding to the acquired 2D-images of the instrument, and to modify the 3D-model representation into an adapted 3D-model representation in order to optimize matching of the 2D-model images to the acquired 2D-images of the instrument, and that the processing unit is further arranged to merge the adapted 3D-model representation of the instrument with the 3D-images of the anatomical structure.

This provides the advantage of increased accuracy and reliability with respect to the 3D-images of the instrument that are merged with the 3D-images of the anatomical structure. By application of the 3D-model representation of the instrument it is furthermore possible to take into account instrument characteristics such as the rigidity of the instrument in different directions.

Also in this second preferred embodiment the accuracy and reliability of the combined images of instrument and anatomical structure can be further enhanced by application of the feature that the apparatus comprises a second C-arm with a second X-ray source and a second X-ray detector for acquiring a second series of 2D-images simultaneously with the first series of 2D-images, and that the processing unit is arranged to carry out the registration of the coordinates of the 3D-model representation in respect of both the first series and the second series of 2D-images of the instrument, and that the processing unit is arranged to derive thereafter an adapted 3D-model representation of the instrument based on both the first series and the second series of 2D-images of the instrument, and to merge this adapted 3D-model representation with the 3D-images of the anatomical structure.

Consistent with the above, the method according to the invention is in a second preferred embodiment characterized in that a 3D-model representation of the instrument is acquired and is registered with the 2D-images of the instrument, and in that 2D-model images of the instrument are derived from said 3D-model representation corresponding to the acquired 2D-images of the instrument, and that said 3D-model representation is adapted to optimize the matching of the 2D-model images with the acquired images of the instrument prior to merging the adapted 3D-model representation of the instrument with the 3D anatomical structure.

A further detailed embodiment thereof is characterized in that a second series of 2D-images is acquired simultaneously with the first series of 2D-images of the instrument bur from a different angle, and that a registration is carried out of the coordinates of the 3D-model representation of the instrument in respect of both the first series and the second series of 2D-images of the instrument, whereafter the 3D-model representation of the instrument is adapted to optimize the matching of said first series and second series of images of the instrument with 2D-model images of the instrument derived from said 3D-model representation, and that thereafter the adapted 3D-model representation of the instrument is merged with the 3D anatomical structure.

The invention is further embodied in software for a computer which is characterized by coding that is arranged for implementing the just mentioned method. The invention is also embodied in a data carrier comprising such software.

The invention will hereafter be further elucidated with reference to a non-limiting example of the apparatus and method according to the invention and with reference to the drawing.

In the drawing

Figure 3:
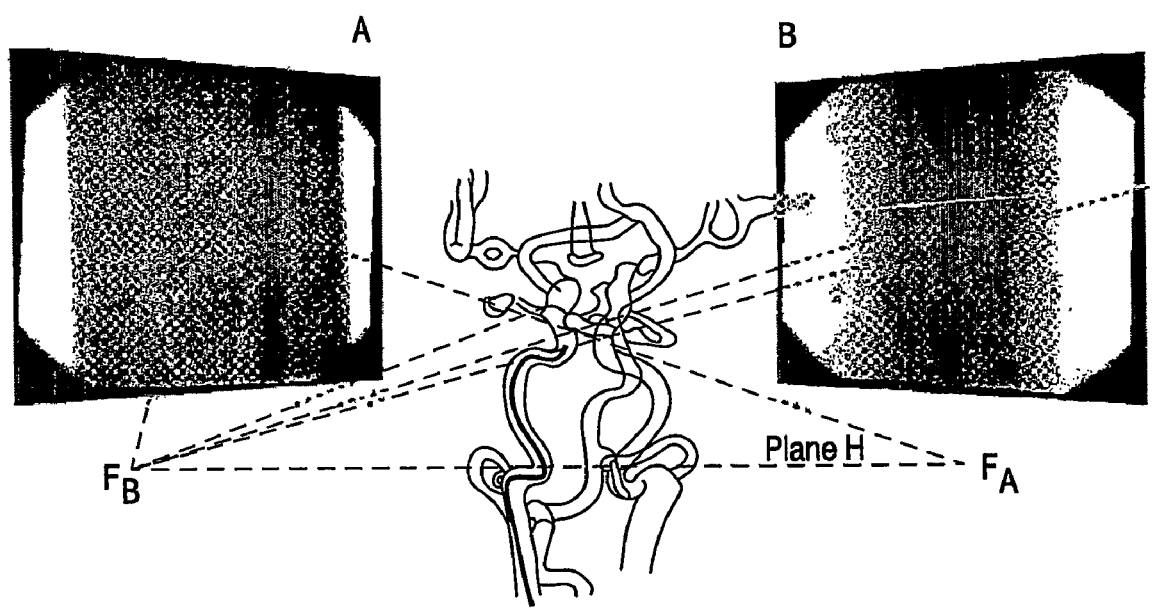

FIG. 3 schematically shows the merger of a 3D-image from the instrument and a predetermined 3D-image of a patient's vascular structure.

FIGS. 4, 5, 6 and 7 show a series of real time 3D-images of an instrument manoeuvering through the vascular structure.

Figure 1:
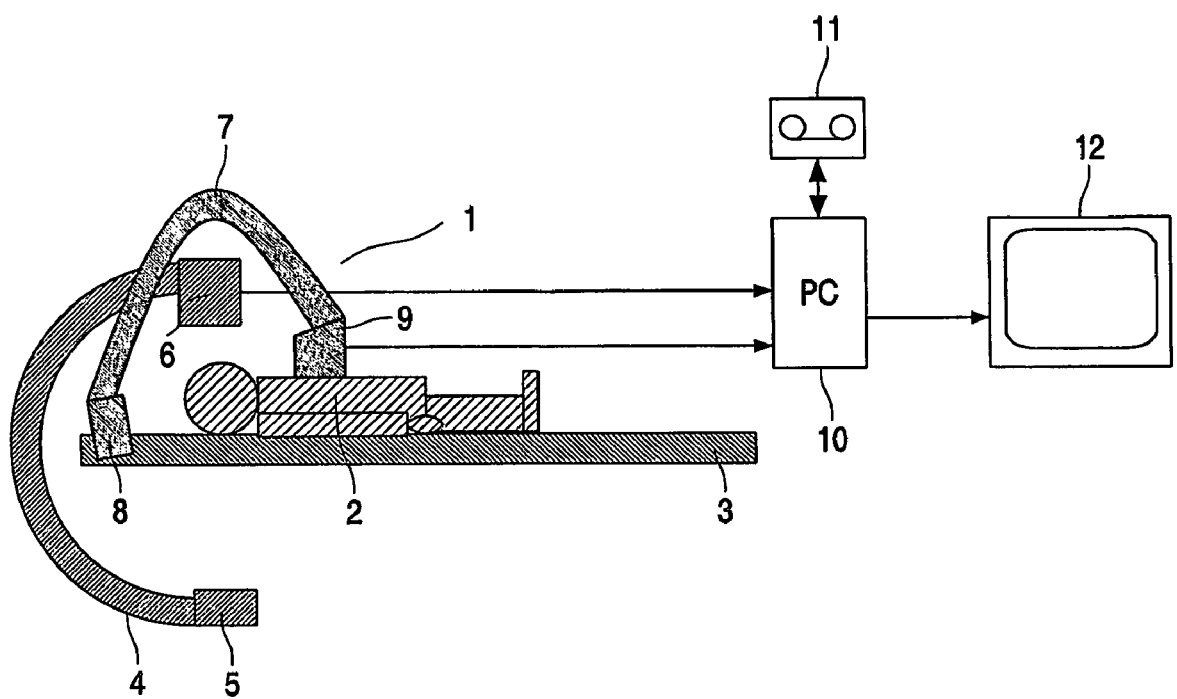
FIG. 1 shows schematically the apparatus according to the invention.

With reference first to FIG. 1 an apparatus 1 is shown for navigating an instrument through a vascular structure of a body volume of a patient 2. The apparatus 1 comprises a table 3 for supporting the patient 2 and in the shown preferred embodiment it comprises a first C-arm 4 with a X-ray source 5 and an image intensifier 6 for acquiring a first series of 2D-images. It further comprises a second C-arm 7 having a X-ray source 8 and an image intensifier 9 for acquiring a second series of 2D-images. Both image intensifiers are connected with a processing unit 10 (a computer) which connects to a memory device 11 and a display unit 12.

Initially in a manner well known in the art 3D-images of the patient's 2 vascular structure are acquired and stored in the memory device 11.

Figure 2:
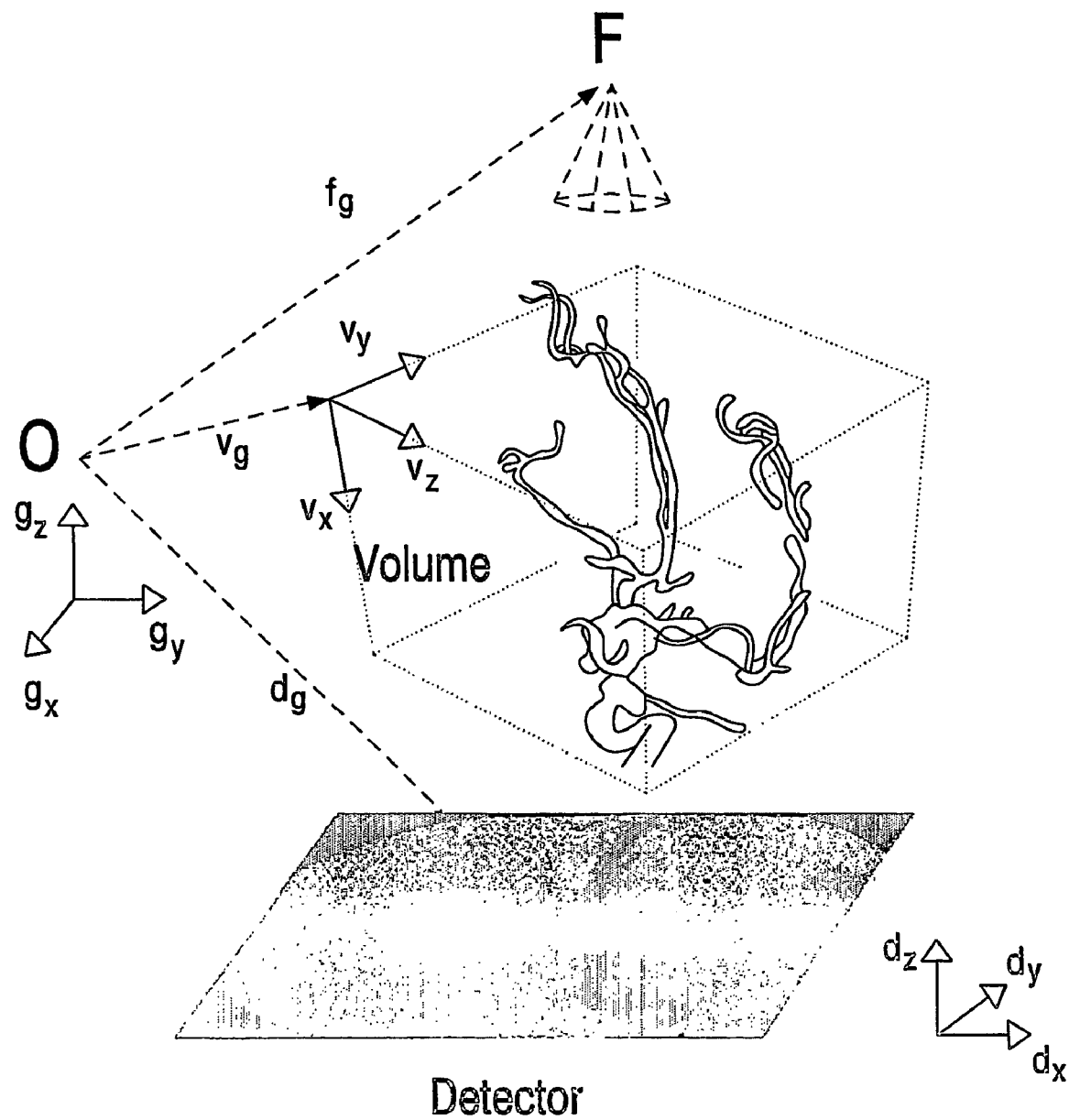
FIG. 2 shows schematically the acquisition of a 2D-image with the aid of the apparatus according to FIG. 1.

When a medical instrument such as a guide wire, a catheter, a stent or otherwise is manoeuvered through the vascular structure of the patient 2 at least one of the C-arms 4, 7 but preferably both arms are used to acquire 2D-images of the instrument. For one C-arm 4 or 7 this is schematically shown in FIG. 2 indicating with 'F' the X-ray source, the patient's body volume shown in the middle whereby the patient's vascular structure is recognizable, and below the patient's body volume a detector for acquiring a 2D-image of the body volume under examination. When the instrument is maneuvered through the vascular structure the X-ray source operates in real time however on a low energy level, which suffices to provide images of the medical instrument.

FIG. 3 relates to biplane imaging of the instrument making use of both C-arms 4 and 7. The middle of the figure shows schematically the vascular structure of the patient in the form of a 3D-image, which is acquired prior to navigating the instrument through the vascular structure.

Making use of both C-arms 4 and 7 a first series of 2D-images of the instrument and a second series of 2D-images of the instrument are acquired simultaneously which is represented by pictures A and B respectively. Picture A represents one image of a first series of images by using X-ray source Fa, picture B represents one image of the second series of images making use of X-ray source Fb. Both the first series and the second series of 2D-images of the instrument are processed by the processing unit 10 to carry out a 2D/3D registration to relate the coordinates of the 2D-images of the instrument, to the coordinates of the 3D-image of the vascular structure. In a first embodiment the 2D-images of the instrument are acquired simultaneously with the images of the vascular structure. In a second more usual embodiment the 3D-images of the anatomical structure are, however, acquired prior to the intervention with the instrument. In this situation it is desirable to immediately precede the imaging of the instrument by a short imaging of the anatomical structure in order to register the images taken during the intervention with the coordinates of the earlier recorded 3D-images of the anatomical structure. This applies to both the first series of 2D-images and the second series of 2D-images of the instrument. FIG. 3 symbolizes that thereafter the two series of 2D-images, which are taken from a different angle, are combined and construed into a 3D representation of the instrument, following which the 3D-image of the instrument is merged with the 3D-image of the vascular structure.

As mentioned hereabove the merger of the 3D-image of the instrument and the 3D-image of the vascular structure can be based both on a single series of images acquired by use of only one C-arm. It is preferred however to make use of both C-arms in order to improve the spatial accuracy and reliability of the 3D-image of the instrument in relation to the 3D-image of the vascular structure.

Also, otherwise a further improvement of the spatial reliability and accuracy of the combined images is obtainable, as will be explained hereafter. In a first embodiment as elucidated hereabove the acquired 2D-images of the instrument are applied directly to derive 3D-images thereof, which are then merged with the 3D-images of the vascular structure.

In a second and more preferred embodiment of the invention the memory device 11 shown in FIG. 1 also holds a pre-determined 3D-model representation of the instrument. This 3D-model representation of the instrument is used by the processing unit 10 in combination with the 2D-images of the instrument that are obtained with either a single C-arm or both C-arms 4 and 7.

To this end the coordinates of the 3D-model representation are registered with the acquired 2D-images of the instrument and subsequently the processing unit 10 carries out calculated projections in relation to the 3D-model representation of the instrument resulting in 2D-model images of the instrument corresponding to the acquired 2D-images of the instrument.

The 3D-model representation is then adapted, usually in an iterative procedure, in order to optimize the matching of the calculated 2D-model images to the acquired 2D-images of the instrument. The eventual 3D-model representation as adapted can then be directly merged with the earlier acquired 3D-images of the vascular structure of the patient. A particularly reliable and accurate reconstruction of the combined images of instrument and vascular structure can thus be obtained.

By executing the method and operating the apparatus according to the invention in real time, a series of 3D-images is acquired as shown in FIGS. 4 to 7.

Figure 4:
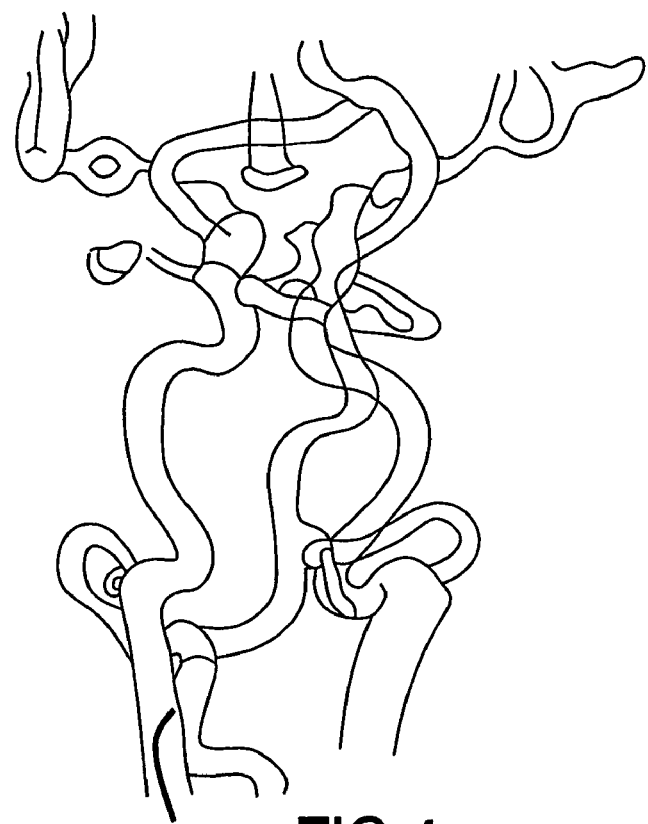
Figure 5:
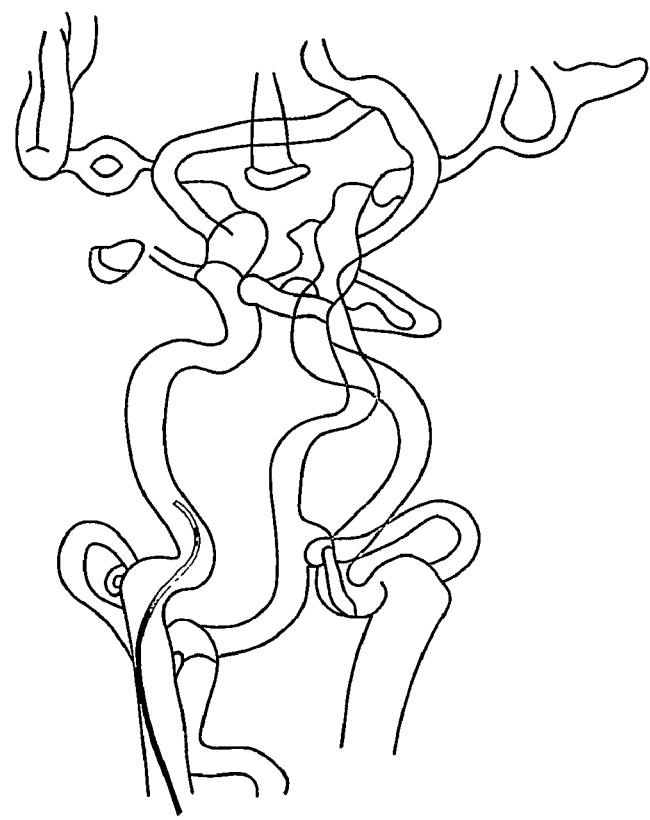
Figure 6:
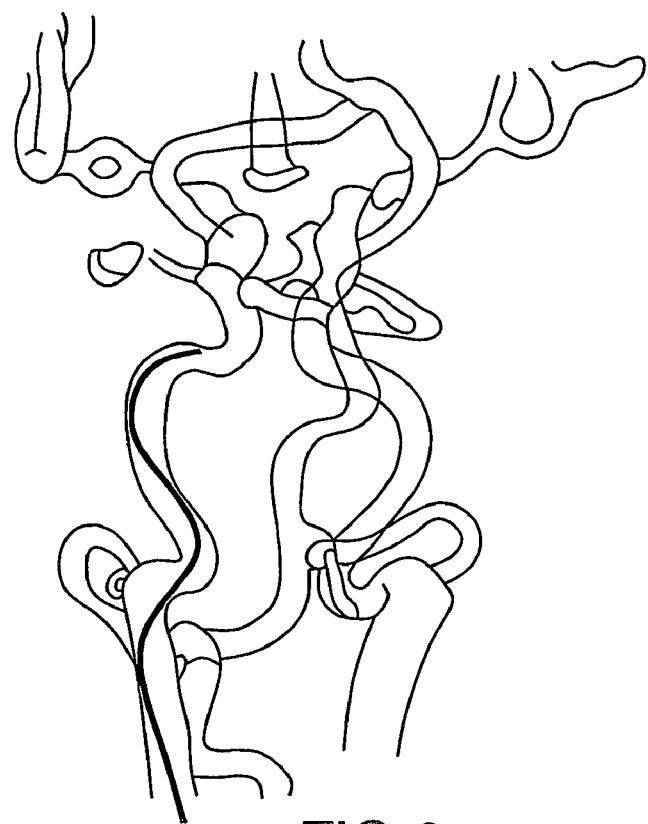
Figure 7:
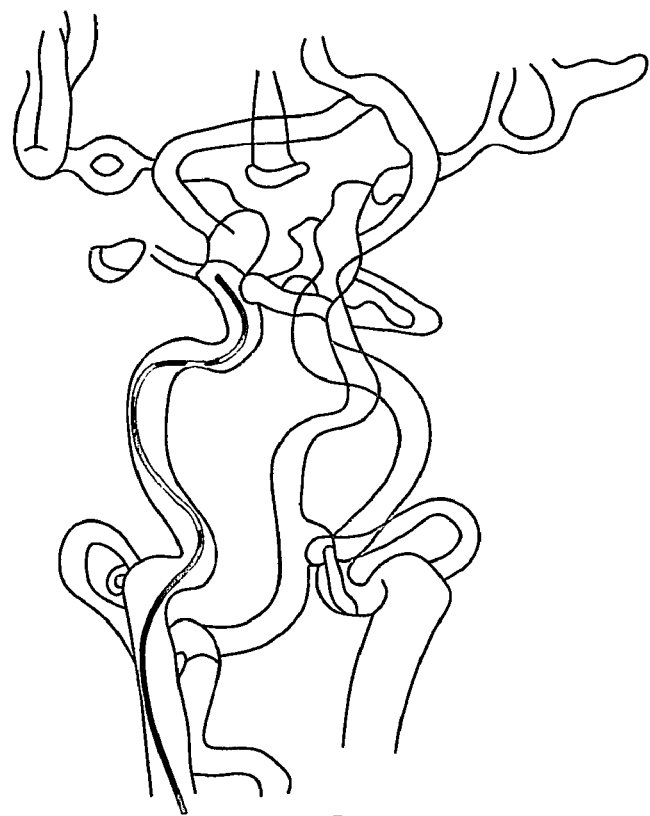

FIG. 4 shows the tip of a guide wire at the entrance portion of the vascular structure of an patient's body volume under examination. FIG. 5 shows same when the guide wire has progressed a little and FIGS. 6 and 7 show same in even further progressed positions.

It is emphasized that the invention can advantageously use any known form of 2D/3D registration to relate the coordinates of the 2D-images of the instrument to the coordinates of the 3D-images of the vascular or any other anatomical structure. For this purpose one could select one of the methods described in the article "A Comparison of Similarity Measures for use in 2D/3D Image Registration" by Graeme P. Penney et al., IEEE Transactions On Medical Imaging, Vol. 17, No. 4 Aug. 1998, pages 586 to 595.

The invention claimed is:

1. An apparatus for navigating an instrument through an anatomical structure of a patient's body volume, the apparatus comprising:
   a table for supporting the patient;
   at least a first C-arm having a first X-ray source and a first X-ray detector configured to acquire a first series of 2D-images of the instrument while manoeuvering through said anatomical structure; and
   a processing unit connected to a memory device, the memory device configured to hold pre-determined 3D-images of the patient's anatomical structure and hold a pre-determined 3D-model representation of the instrument; and
   wherein the processing unit is configured to:
      perform a 2D-3D registration to relate coordinates of the 2D-images of the instrument to coordinates of the 3D-images of the anatomical structure
      perform a 2D-3D registration to relate coordinates of the 3D-model representation of the instrument with the coordinates of the 2D-images of the instrument,
      calculate projections of the 3D-model representation to generate 2D-model images of the instrument corresponding to the acquired 2D-images of the instrument,
      modify the 3D-model representation in order to optimize matching of the 2D-model images to the acquired 2D-images of the instrument to derive an adapted 3D-model representation of the instrument, and
      merge the adapted 3D-model representation of the instrument with the 3D-images of the anatomical structure to provide merged 3D-images of the instrument manoeuvering through said anatomical structure.

2. The apparatus according to claim 1, further comprising:
   a second C-arm with a second X-ray source and a second X-ray detector for acquiring a second series of 2D-images of the instrument simultaneously with the first series of 2D-images of the instrument;
   wherein the processing unit is configured to:
      register the coordinates of the 3D-model representation respective to both the first series and the second series of 2D-images of the instrument, and
      derive the adapted 3D-model representation of the instrument based on both the first series and the second series of 2D-images of the instrument.

3. A method for navigating an instrument through an anatomical structure of a patient's body volume, the method comprising:
   acquiring a first series of 2D-images of the instrument while maneuvering the instrument through the anatomical structure;
   acquiring 3D images of the patient's anatomical structure;
   acquiring a 3D-model representation of the instrument; and
   processing the 2D-images of the instrument and 3D-images of the patient's anatomical structure to generate merged 3D-images of the instrument manoeuvering through the anatomical structure by performing the steps of:
      registering the acquired 3D-images of the anatomical structure with the 2D images of the instrument
      registering the acquired 3D-model representation of the instrument with the 2D-images of the instrument,
      deriving 2D-model images of the instrument from said 3D-model representation of the instrument, the 2D-model images corresponding to the acquired 2D-images of the instrument,
      modifying said 3D-model representation to optimize matching of the derived 2D-model images with the acquired 2D-images of the instrument, the modifying generating an adapted 3D-model representation of the instrument, and
      merging the adapted 3D-model representation of the instrument with the 3D images of the patient's anatomical structure to generate the merged 3D-images of the instrument manoeuvering through the anatomical structure.

4. The method according to claim 3, further comprising:
   acquiring a second series of 2D-images of the instrument simultaneously with the acquiring of the first series of 2D-images of the instrument, the second series of 2D-images being acquired from a different angle compared with the first series of 2D images,
   wherein:
      the registering includes registering the coordinates of the 3D-model representation of the instrument respective to both the first series and the second series of 2D-images of the instrument, and
      the modifying includes modifying the 3D-model representation of the instrument to optimize the matching of said first series and second series of 2D-images of the instrument with the 2D-model images of the instrument derived from said 3D-model representation.

5. A non-transitory computer readable medium having, stored thereon, computer executable software for navigating an instrument through an anatomical structure of a patient's body volume, the software comprising instructions for causing a computer to implement the steps of:
receiving a first series of 2D-images of the instrument while manoeuvering through the anatomical structure;
receiving 3D images of the patient's anatomical structure;
receiving a 3D-model representation of the instrument and
processing the 2D-images of the instrument the 3D-images of the patient's anatomical structure to generate merged 3D-images of the instrument manoeuvering through the anatomical structure by performing the steps of:
registering the 2D-images of the instrument with the 3D-images of the anatomical structure,
registering the 3D-model representation of the instrument with the 2D-images of the instrument,
deriving 2D-model images of the instrument from said 3D-model representation, the 2D-model images corresponding to the received 2D-images of the instrument, and
modifying the 3D-model representation in order to optimize matching of the 2D-model images with the received 2D-images of the instrument to generate an adapted 3D-model representation of the instrument, and
merging the adapted 3D-model representation of the instrument with the 3D images of the patient's anatomical structure to generate the merged 3D-images of the instrument manoeuvering through the anatomical structure.

6. The software stored on the non-transitory computer readable medium according to claim 4, wherein said first series of 2D-images of the instrument and a second series of 2D-images of the instrument are received simultaneously, but from a different angle, by the receiving step, and wherein:
the registering includes registering the coordinates of the 3D-model representation of the instrument respective to both the first series and the second series of 2D-images of the instrument, and
the modifying includes adapting the 3D-model representation of the instrument in order to optimize the matching of said first series and second series of images of the instrument with the 2D-model images of the instrument derived from said 3D-model representation.

7. A method comprising:
processing 2D-images of an instrument acquired from one or more viewing angles during maneuvering of the instrument through an anatomical structure of a patient's body volume to generate 3D-images of the instrument manoeuvering through the anatomical structure by performing the steps of:
registering a 3D-model representation of the instrument with the acquired 2D-images of the instrument,
calculating projections of the 3D-model representation to derive 2D-model images of the instrument from the one or more viewing angles, and
modifying the 3D-model representation to optimally match the derived 2D-model images and the acquired 2D-images of the instrument to derive an adapted 3D-model representation of the instrument, and
merging the adapted 3D-model representation of the instrument and a 3D-image of the patient's anatomical structure to generate the 3D-images of the instrument maneuvering through the anatomical structure.

8. The method as set forth in claim 7, wherein the 2D-images of the instrument are acquired from two different viewing angles during the maneuvering of the instrument through the anatomical structure of the patient's body volume.

9. The method as set forth in claim 7, further comprising:
maneuvering the instrument through the anatomical structure of the patient's body volume; and
during the maneuvering, acquiring the 2D-images of the instrument from one or more viewing angles.

10. The method as set forth in claim 7, wherein the adapting generates an adapted 3D-model representation of the instrument and the 3D-images of the instrument manoeuvering through the anatomical structure comprise at least the adapted 3D-model representation of the instrument.

11. The method as set forth in claim 7, wherein the processing includes iteratively repeating the projecting and the adapting to iteratively optimize the match of the projected 2D-model images and the acquired 2D-images of the instrument.

12. A non-transitory computer readable medium having, stored thereon, computer executable software comprising instructions for causing a computer to perform the method of claim 7.

* * * * *